United States Patent [19]

Nohira et al.

[11] Patent Number: 4,999,130

[45] Date of Patent: Mar. 12, 1991

[54] OPTICALLY ACTIVE COMPOUND, PROCESS FOR PRODUCING SAME AND LIQUID CRYSTAL COMPOSITION CONTAINING SAME

[75] Inventors: Hiroyuki Nohira, Urawa; Takashi Kimura, Utsunomiya; Tetsuya Abe, Kitaibaraki; Yoko Yamada, Atsugi; Kazuhige Yamagishi, Kusatsu, all of Japan

[73] Assignees: Canon Kabushiki Kaisha; Yamakawa Chemical Industry Co., Ltd., both of Tokyo, Japan

[21] Appl. No.: 572,301

[22] Filed: Aug. 27, 1990

Related U.S. Application Data

[63] Continuation of Ser. No. 269,616, Nov. 10, 1988, abandoned.

[30] Foreign Application Priority Data

Nov. 11, 1987 [JP] Japan ................................ 62-283079
Feb. 23, 1988 [JP] Japan ................................ 63-038617

[51] Int. Cl.$^5$ ........................ C09K 19/52; C07C 31/34
[52] U.S. Cl. ........................... 252/299.01; 252/299.41; 252/299.67; 252/299.63; 252/299.66; 252/299.6; 252/299.65
[58] Field of Search ........... 252/299.01, 299.6, 299.63, 252/299.66, 299.61, 299.65, 299.67; 350/350 R, 350 S; 558/443, 451, 354

[56] References Cited

U.S. PATENT DOCUMENTS

| | | | |
|---|---|---|---|
| 4,576,732 | 3/1986 | Isogai et al. | 252/299.67 |
| 4,592,858 | 6/1986 | Higuchi et al. | 252/299.66 |
| 4,613,209 | 9/1986 | Goodby et al. | 252/299.67 |
| 4,695,650 | 9/1987 | Walba et al. | 252/299.67 |
| 4,723,005 | 2/1988 | Huynh-Ba et al. | 252/299.63 |
| 4,725,688 | 2/1988 | Taguchi et al. | 252/299.61 |
| 4,728,458 | 3/1988 | Higuchi et al. | 252/299.67 |
| 4,732,694 | 3/1988 | Higuchi et al. | 252/299.66 |
| 4,777,280 | 10/1988 | Eidman et al. | 252/299.67 |
| 4,786,730 | 11/1988 | Shibata et al. | 252/299.61 |
| 4,798,680 | 1/1989 | Nohira et al. | 252/299.01 |
| 4,820,839 | 4/1989 | Krause et al. | 252/299.61 |

FOREIGN PATENT DOCUMENTS

| | | | |
|---|---|---|---|
| 239444 | 9/1987 | European Pat. Off. | 252/299.65 |
| 248335 | 12/1987 | European Pat. Off. | 252/299.61 |
| 3525015 | 1/1986 | Fed. Rep. of Germany | 252/299.66 |
| 3515373 | 11/1986 | Fed. Rep. of Germany | 252/299.61 |
| 3638026 | 5/1988 | Fed. Rep. of Germany | |
| 63-22042 | 1/1988 | Japan | 252/299.01 |
| 63-104949 | 5/1988 | Japan | 252/299.01 |
| 8705018 | 8/1987 | World Int. Prop. O. | 252/299.01 |
| 8706021 | 10/1987 | World Int. Prop. O. | 252/299.01 |
| 8705017 | 8/1988 | World Int. Prop. O. | 252/299.01 |
| 8808019 | 10/1988 | World Int. Prop. O. | 252/299.61 |

OTHER PUBLICATIONS

Drug Research, vol. 228 (II), No. 7 (1978), 1048:56.
Chem. Abs., vol. 31, No. 4 (Feb. 20, 1937).
Chem. Abs., vol. 107, No. 4 (Jul. 27, 1987) 31339z.
Taniguchi, H. et al., Japan J. Appl. Phys., vol. 26, Suppl. 26-2, pp. 101-103, 1987.
Huppatz, John L., et al., Pestic. Sci., vol. 13(1), pp. 78-84 (1982).
Cas, Registry Nos. 82295—(41-8), (40-7), (38-3), (37-2), 1982.

*Primary Examiner*—Robert L. Stoll
*Assistant Examiner*—Chhaya Sayala
*Attorney, Agent, or Firm*—Fitzpatrick, Cella, Harper & Scinto

[57] ABSTRACT

An optically active 2-cyano-2-methyl-alkanoic acid represented by the formula:

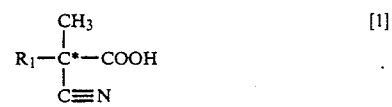

is produced by optical resolution of the corresponding racemic mixture thereof with an optically active amine and is reduced to provide an optically active 2-cyano-2-methyl-1-alkanol represented by the formula:

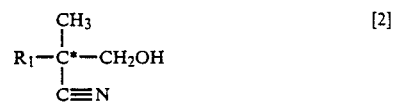

wherein $R_1$ denotes an alkyl groups having 3-10 carbon atoms, $R_2$ denotes an alkyl group having 2-10 carbon atoms and C* denotes an asymmetric carbon atom. These compounds are characterized by having a CN group with a large dipole moment directly attached to an asymmetric carbon atom and are effective for controlling the liquid crystal state of a liquid crystal composition when added thereto.

8 Claims, No Drawings

OPTICALLY ACTIVE COMPOUND, PROCESS FOR PRODUCING SAME AND LIQUID CRYSTAL COMPOSITION CONTAINING SAME

This application is a continuation of application Ser. No. 269,616, filed Nov. 10, 1988, now abandoned.

FIELD OF THE INVENTION AND RELATED ART

The present invention relates to a novel optically active compound, a process for producing the same, and a liquid crystal composition containing the same.

There have been known various types optical devices characterized by having optical activities as will be exemplified as follows:

(1) Those utilizing a cholesteric-nematic phase transition in a liquid crystal state (J.J. Wysoki, A. Adams and W. Haas: Phys. Rev. Lett., 20, 10204 (1968);

(2) Those utilizing a guest-host effect of the White-Taylor type in a liquid crystal state (D.L. White and G.N. Taylor: J. Appl. Phys., 45, 4718 (1974)):

(3) Those utilizing a ferroelectric liquid crystal effect of a chiral smectic C phase, H phase, F phase, I phase or G phase (N.A. Clark and S.T. Lagerwall: Appl. Phys. Lett., 36 899 (1980));

(4) Others including notch filters or bond path filters utilizing selective scattering characteristics of a material having a cholesteric phase in the liquid crystal state when fixed in a matrix (F.J. Kahn: Appl. Phys. Lett., 18, 231 (1971)); and circular polarization beam splitters utilizing circular polarization characteristics (S.D. Jacobs, SPIE, 37, 98 (1981)).

These optical devices are important as display devices and modulation devices, while the explanation of the individual systems is left to the respective references and omitted.

Functional materials constituting these optical devices contain an optically active compound or substance as a major component thereof or as a component which is used in a relatively small proportion but constitutes a functionally important part. For example, H. Arnold, Z. Phys. Chem., 226, 146 (1964) discloses to add another optically active substance or mesomorphic compound to an optical device material, particularly a liquid crystal material, to control the kind of a liquid crystal phase or the temperature range in the resultant liquid crystal state. Further, it is also expected to add a compound having a large dipole moment to a liquid crystal material driven by an electric field response to obtain a liquid crystal material having a better electric field responsive characteristic.

However, optically active substances known heretofore are generally not easy to change the length of a group introduced thereinto, so that most of them are not suitable for controlling the liquid crystal state.

Further, few compounds having a group with a large dipole moment directly attached to an asymmetric carbon atom have been known, so that it has not been possible to obtain a sufficient improvement in electric field response characteristic of an optical device as described above.

SUMMARY OF THE INVENTION

In view of the above circumstances, it is a principal object of the present invention to provide an optically active substance which is effective for controlling a liquid crystal state and has a group having a large dipole moment directly attached to an asymmetric carbon atom, and also a liquid crystal composition containing such an optically active substance.

A more specific object of the present invention is to provide a compound having a group with a large dipole moment attached to an asymmetric carbon atom and showing an excellent electric field response characteristic.

Another object of the present invention is to provide an optically active compound capable of readily changing the length of the alkyl chain and therefore capable of controlling a kind of liquid crystal phase to be developed in the liquid crystal state and a temperature range therefor as shown by H. Arnold: Z. Phys. Chem., 226, 146 (1964), and a liquid crystal composition containing at least one of such optically active compounds.

The present invention provides an optically active 2-cyano-2-methyl-alkanoic acid represented by the formula:

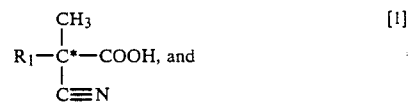

an optically active 2-cyano-2-methyl-1-alkanol represented by the formula:

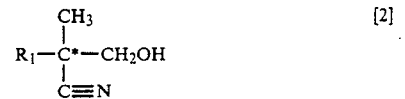

which is obtained by reducing an optically active 2-cyano-2-methyl-alkanoic acid of the formula:

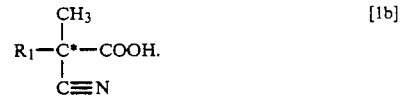

In the above formulas [1], [1b] and [2], $R_1$ denotes an alkyl group having 3–10 carbon atoms, $R_2$ denotes an alkyl group having 2–10 carbon atoms, and C* denotes an asymmetric carbon atom.

The present invention also provides liquid crystal compositions containing the above mentioned optically active compounds.

The optically active compound represented by the formulas [I] and [2] are compounds which can be widely utilized, because they have a carboxylic group or a hydroxyl group connected to an asymmetric carbon atom through a methylene group so that they can be readily converted without losing their optical activity into various derivatives through an ester bond, an ether bond, an urethane bond, a carbonate bond, etc.

These optically active compounds represented by the formulas [1] and [2], however, have not been known heretofore. As a result of our intensive study, we have succeeded in synthesis of these compounds and arrived at the present invention.

The present invention also provides processes for producing the compounds of the above formulas [1] and [2]. According to the methods, ethyl cyano-acetate, for example, is used as a starting material to produce a racemic mixture of the compound of the formula [1], which is then subjected to optical resolution to produce an optically active compound of the formula [1]. Further, an optically active compound of the formula [2] may be produced by reducing a compound of the above formula [1b] prepared in the above-described manner.

Thus, the present invention also provides a process for producing an optically active 2-cyano-2-methyl-alkanoic acid of the above formula [1], comprising subjecting a racemic 2-cyano-2-methyl-alkanoic acid of the formula:

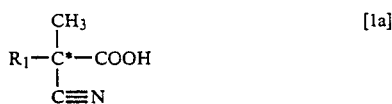

to optical resolution with an optically active amine wherein $R_1$ denotes an alkyl group having 3–10 carbon atoms, and $C^*$ denotes an asymmetric carbon atom; and a process for producing an optically active 2-cyano-2-methyl-1-alkanol of the above formula [2], comprising reducing an optically active 2-cyano-2-methyl-alkanoic acid represented by the formula:

wherein $R_2$ denotes an alkyl group having 2–10 carbon atoms, and $C^*$ denotes an asymmetric carbon atom.

The optically active compounds represented by the formulas [1] and [2] are not only a useful optically active intermediate but also a useful liquid crystal component by themselves. For example, when they are added in a very small amount in a nematic liquid crystal composition for a TN (twisted nematic)-type display device, they may effectively prevent the occurrence of a fringe pattern (reverse domain) to uniformize the display.

Thus, the present invention also provides a liquid crystal composition comprising a mesomorphic compound or liquid crystal and an optically active compound represented by the formula [1] or [2].

DETAILED DESCRIPTION OF THE INVENTION

In order to produce an optically active 2-cyano-2-methyl-1-alkanoic acid of the formula [1], ethyl cyanoacetate may be used as a starting material to produce a compound of the following formula [3] according to a method described in Organic Synthesis Col. vol. III, page 385;

Then, the compound of the formula [3] is methylated with methyl iodide according to a method similar to one described in Organic Reaction, vol. 9, page 161, thereby to produce a compound of the following formula [4]:

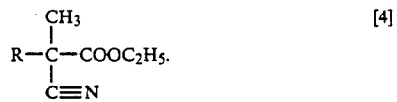

Then, the compound of the formula [4] is hydrolyzed to obtain a racemic 2-cyano-2-methyl-alkanoic acid of the above-mentioned formula [1a].

The racemic compound is subjected to optical resolution by using a basic optical resolving agent, such as (+) or (−) cis-2-benzylaminocyclohexyl-methanol, α-methylbenzylamine, α-ethylbenzylamine, α-(p-tolyl)ethylamine, 1-phenyl-2-(p-tolyl)ethylamine, 1-phenyl-2-(p-tolyl)ethylamine, 1-(1-napthyl)ethylamine, 1-(2-naphthyl)ethylamine, or 2-amino-1,2-diphenylethanol, thereby to obtain an optically active compound of the above formula [1].

A compound of the above formula [1b] may be produced similarly as the compound of the formula [1] and reduced to provide an optically active compound of the above formula [2].

The above-mentioned series of reactions may be summarized by the following reaction scheme:

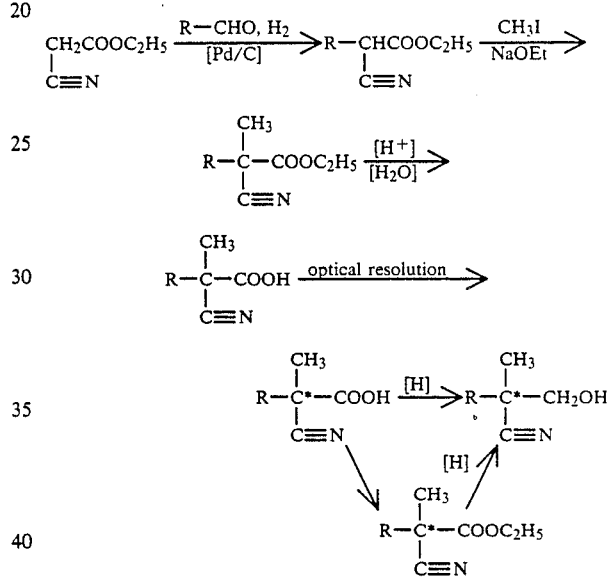

The optically active compounds according to the present invention represented by the formulas [1] and [2] can have a wide variety of R by changing the number of carbon atoms in the alkane moiety in an alkyl aldehyde reacted with the starting ethyl cyanoacetate but those having an alkyl R of 2–10 carbon atoms, preferably 3–10 carbon atoms, more preferably 3–8 carbon atoms, further preferably 4–6 carbon atoms, are provided by the present invention.

As has been briefly mentioned hereinbefore, the optically active compound represented by the formula [1] or [2] may be used instead of a conventionally used optically active compound such as a hydrocarbon chain derivative, an amino acid derivative, a camphor derivative, or a cholesterol derivative, and may be connected with another intermediate through ester bond, ether bond, urethane bond, carbonate bond, etc., by using a releasable carboxylic or hydroxyl group. For this reason, the optically active compound is not only useful as an intermediate for producing functional materials constituting optical devices, but also useful as an intermediate for synthesizing various natural optically active compounds.

Further, the optically active compound represented by the formula [1] or [2] is effectively used for preventing generation of reverse domain in a TN-type cell by adding it into a nematic liquid crystal. In this case, the optically active compound of the formula [1] or [2] may preferably be used in a proportion of 0.01-50 wt. %, preferably 0.1-10 wt. %, of the resultant liquid crystal composition.

Further, the optically active compound may be used to form a chiral nematic liquid crystal composition for use in a phase-transition type liquid crystal device or guest-host type liquid crystal device of the White-Taylor type by adding it into a nematic or chiral nematic liquid crystal In this case, the optically active compound of the formula [1] or [2] may preferably be used in a proportion of 0.01-80 wt. %, more preferably 0.1-20 wt. %, of the resultant liquid crystal compostion.

Further, the optically active compound of the formula [1] or [2] may be added to a liquid crystal material showing a ferroelectric chiral smectic liquid crystal state by itself in a proportion of 0.01-80 wt. %, preferably 1-50 wt. %, of the resultant liquid crystal composition to form a liquid crystal composition with an improvement in characteristics such as durability.

Furthermore, the optically active compound of the formula [1] or [2] may be added to a smectic liquid crystal including those shown below at (1)-(5) with structural formulas and phase transition temperature (°C.), to provide a liquid crystal composition showing a ferroelectric chiral smectic phase. In this case, the optically active compound of the formula [1] or [2] may be used in a proportion of 0.01-80 wt. %, preferably 1-50 wt. %, of the resultant liquid crystal composition. When the optically active compound of the formula [1] [2] is added to provide a chiral smectic liquid crystal composition in the manner as described above, the liquid crystal composition can have a large spontaneous polarization, a shorter response time, and a lower threshold voltage.

(1)

$C_8H_{17}O$—⬡—⬡—COO—⬡—$OC_9H_{19}$ (4-nonyloxyphenyl)-4'-octyloxybiphenyl-4-carboxylate Cryst. $\underset{74}{\overset{107}{\rightleftarrows}}$ SmB $\overset{117}{\rightleftarrows}$ SmC $\overset{160}{\rightleftarrows}$ SmA $\overset{195}{\rightleftarrows}$ Iso.

(2)

$C_{10}H_{21}O$—⬡—N=N—⬡—$OC_{10}H_{21}$
               ‖
               O 4,4'-decyloxyazoxybenzene Cryst. $\overset{77}{\rightarrow}$ SmC $\overset{120}{\rightleftarrows}$ N $\overset{123}{\rightleftarrows}$ Iso.

(3)

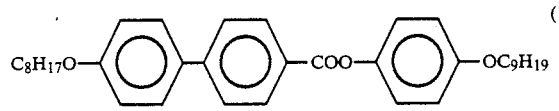

2-(4'-hexyloxyphenyl)-5-(4-hexyloxyphenyl)-pyrimidine

Cryst. $\overset{120}{\rightarrow}$ SmC $\overset{189}{\rightleftarrows}$ SmA $\overset{216}{\rightleftarrows}$ Iso.

(4)

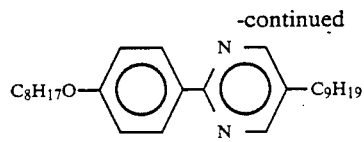

2-(4'-octyloxyphenyl)-5-nonylpyrimidine

Cryst. $\overset{33}{\rightarrow}$ SmC $\overset{60}{\rightleftarrows}$ SmA $\overset{75}{\rightleftarrows}$ Iso.

(5)

$C_8H_{17}O$—⬡—COO—⬡—$OC_5H_{11}$

4'-pentyloxyphenyl-4-octyloxybenzoate

Cryst. $\overset{58}{\rightarrow}$ SmC $\overset{64}{\rightarrow}$ SmA $\overset{66}{\rightarrow}$ N $\overset{85}{\rightarrow}$ Iso.

Herein, the symbols respectively denote the following phases:
Cryst.:crystal phase
SmA:smectic A phase
SmB:smectic B phase
SmC:smectic C phase
N:nematic phase
Iso.:isotropic phase

EXAMPLES

Hereinafter, the present invention will be more specifically explained with reference to specific examples of production.

EXAMPLE 1

Optical resolution of 2-cyano-2-methylhexanoic acid.
4.62 g (21.1 mM) of (−)-cis-2-benzylaminocyclohexylmethanol (hereinafter abbreviated as "(−)-cis amine") was dissolved under heating in 6.2 ml of a mixture solvent of benzene-hexane (2:3). Thereto, 4.36 g (28.1 mM) of (±)-2-cyano-2-methylhexanoic acid (hereinafter abbreviated as "(±)-CMHA") was added to be dissolved therein under heating, followed by standing overnight in a refrigerator. The precipitated crystal was recovered by filtration to obtain 6.98 g of crude (−)-cis amine.(+)-CMHA salt. The salt was subjected to two times of recyctallization from the above mixture solvent to obtain 2.41 g (6.44 mM) of purified (−)-cis amine.(+)-CMHA salt. The yield based on the assumption of half the (±)-CMHA used being taken as 100% was 45.8% m.p. (melting point):1-21-125° C., $[α]_D^{14}$ −8.8 degrees (c1, methanol).

The salt was dissolved in 1N-aqueous sodium hydroxide solution, followed by extraction of (−)-cis amine with ether for removal. Then, the aqueous layer was acidified to pH 1 by adding conc. hydrochloric acid, followed by extraction of (+)-CMHA with ether. The resultant ether solution was dried on sodium sulfate, followed by removal of the solvent by distillation to obtain 0.96 g (6.2 mM) of (+)-CMHA. The yield based on the assumption of half the (±)-CMHA used being taken as 100% was 44.1%. $[α]_D^{21}$ +6.5 degrees (c 1.857, methanol).

The thus-obtained (+)-CMHA was synthesized into an amide with optically active naphthylethylamine, and the optical purity of the amide was examined by high-speed liquid chromatography.

(−)-CMHA may be recovered by using (+)-cis amine instead of (−)-cis amine in the above-described operation.

EXAMPLE 2

Production of (+)-2-cyano-2-methyl-1-hexanol

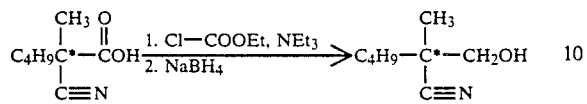

A mixture of 1.25 g (8.1 mM) of (−)-2-methylhexanoic acid ($[\alpha]_D^{26}$ −6.15 degrees (c 1.073, methanol)), 20 ml of dry tetrahydrofuran and 0.90 g (8.9 mM) of dry triethylamine was cooled on an ice bath, and 0.84 g (8.1 mM) of ethyl chloroformic acid was added dropwise thereto in 5 minutes, followed by 1 hour of stirring at 0° C. A white salt precipitated at this time was removed by filtration. To a mixture of 0.46 g (12.1 mM) of sodium borohydride and 8 ml of distilled water under stirring at 0° C., the above filtrate was added dropwise in 20 min., followed by stirring at room temperature for 3 hours. After the reaction, 2N-hydrochloric acid was added to give pH 1, and the organic layer was separated. The remaining aqueous layer was subjected to extraction with ether, and the ether extract was mixed with the organic layer. The mixture was washed with 1N-sodium bicarbonate aqueous solution and dried on sodium sulfate. After the removal of solvent by distillation, the product was subjected to distillation by a Kugelrohr distiller. At 95° C./4 mmHg, (+)-2-cyano-2-methyl-1-hexanol was obtained in an amount of 0.55 g (Yield:48.5%), $[\alpha]_D^{26}$ +0.66 degree (c 1.823, ether).

EXAMPLE 3

A solution of 915 mg (5 mM) of (+)-2-cyano-2methylhexanoic acid-ethyl-ester ($[\alpha]_D$ +2.2 degrees (c 2.782, methanol)) in 8 ml of dry tetrahydrofuran was added dropwise to a mixture of 423 mg (10 mM) of anhydrous lithium chloride and 379 mg (10 mM) of sodium borohydride under stirring at room temperature. Then, 17 ml of dry ethanol was added thereto, followed by reaction for 18 hours at room temperature. After the reaction, the reaction mixture was cooled on an ice bath and acidified to pH 4 by adding 10% citric acid. A precipitate formed at that time was removed by filtration, and the solvent in the filtrate was removed by reduced pressure distillation. Then, 5 ml of distilled water was added to the remaining product, and the mixture was subjected to extraction with dichlocomethane. The organic layer was dried on sodium sulfate, and the solvent was distilled off under reduced pressure, followed further by distillation to obtain (−)-2-cyano-2-methylhexanol. Yield:63.8%, $[\alpha]_D$ −1.2 degree (c 2.393, methylene chloride).

EXAMPLE 4

Optically active 2-cyano-2-methylpentanoic acid was prepared along the following reaction scheme:

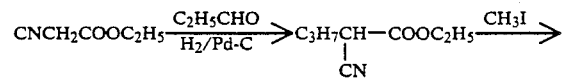

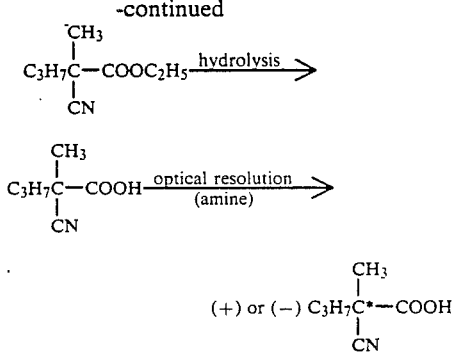

STEP 1

Production of ethyl 2-cyanopentanoate.

Into a 300-ml round-bottomed flask with ground fitting, 28.25 g (250 mM) of ethyl cyanoacetate and 17.05 g (294 mM) of propionaldehyde were weighed, and 5 0 g of catalyst palladium/carbon (5%) and 40 ml of glacial acetic acid (solvent) were added thereto. Then, a solution of 1.0 ml of piperidine and 10 ml of glacial acetic acid separately measured were added thereto. Then, the flask was set in an ordinary pressure hydrogenation apparatus, and after replacement with hydrogen in the system, hydrogenation was caused to proceed under stirring with a magnetic stirrer.

The reaction was stopped after 12.5 hours when the absorption of hydrogen exceeded the theoretical volume of 6082 ml( 250 mM/23.5° C.) and ceased. The reaction liquid filtrated through a pleated filter paper to remove the palladium/carbon, which was then washed with 30 ml of benzene. The filtrate was well washed with 30 ml of saturated saline water and 50 ml of distilled water, and the resultant organic layer was dried on anhydrous sodium sulfate, followed by distilling-off of the solvent. By distillation under a reduced pressure, 33.95 g (219 mM) of ethyl 2-cyanopentanoate was obtained. Yield:87.6%, b.p.:80° C./3 mmHg.

STEP 2

Production of ethyl 2-cyano-2-methylpentanoate.

Into a 200 ml two-necked round-bottom flask with ground fitting, 45 ml of dry ethanol was placed, and 2.05 g (89.1 mM) of sodium cut into small pieces was added. The mixture was stirred by a magnetic stirrer under cooling on an ice bath.

After the sodium was completely reacted to form sodium ethoxide, 12.01 g (77.5 mM) of ethyl 2-cyanopentanoate was added dropwise in about 5 min. through a dropping funnel and 11.00 g (77.5 mM) of sodium iodide was added dropwise in about 2 min. The mixture was stirred for 6 hours at 50° C. on an oil bath, followed by distilling-off of the solvent from the reaction liquid and addition of 20 ml of 1N-HCl. The mixture was transferred to a separating funnel and subjected to three times of extraction with 30 ml of benzene, followed by drying on anhydrous sodium sulfate, distilling-off of the solvent, and reduced-pressure distillation to obtain 10.43 g (61.7 mM) of ethyl 2-cyano-2-methylpentanoate. Yield:79.6%, b.p.:115° C./27 mmHg.

STEP 3

Production of 2-cyano-2-methylpentanoic acid.

In a 200 ml two-necked round-bottom flask with ground fitting, 16.00 g (94.7 mM) of ethyl 2-cyano-2-methylpentanoate and 90 ml of ethanol were placed. To the mixture under stirring with a magnetic stirrer, a solution of 10.8 g (270 mM) of sodium hydroxide in 35 ml of distilled water was added dropwise. The mixture was stirred for 5 hours at room temperature, followed by removal of the solvent and addition of 3N-HCl until the solution reacted pH 1. The reaction mixture was transferred to a separating funnel, followed by three times of extraction with 50 ml of diethyl ether and washing with 50 ml of distilled water. The organic layer was dried on anhydrous sodium sulfate, followed by distilling-off of the solvent and reduced-pressure distillation to obtain 12.61 g (89.4 mM) of 2-cyano-2-methylpentanoic acid. Yield:94.4%, b.p.:120° C./2 mmHg.

STEP 4

Optical resolution of 2-cyano-2-methylpentanoic acid.

7.01 g (32 mM) of (−)-cis-2-benzylaminocyclohexylmethanol was dissolved in 32 ml of ethanol, and (±)-2-cyano-2-methylpentanoic acid was added thereto, followed by stirring under heating to form a uniform solution.

The solution was left to stand at room temperature for cooling to precipitate a crystal, which was recovered by filtration, dried in a desiccator and then subjected to three times of recrystallization from ethanol. The thus-obtained crystal was placed in a 100 ml round-bottomed flask, and 20 ml of diethyl ether and 15 ml of 1N-sodium hydroxide aqueous solution were added thereto, followed by stirring until the crystal was completely dissolved. The mixture was subjected to liquid separation by means of a separating funnel. The aqueous layer was acidified with addition of 2N-hydrochloric acid, followed by drying on anhydrous sodium sulfate and distilling-off of the solvent to obtain 1.44 g (10.2 mM) of (+)-2-cyano-2-methylpentanoic acid. Yield:51% (half the amount of the starting material being taken as 100%), $[\alpha]_D$ +8.3 degrees, $[\alpha]_{435}$ +17.7 degrees (c1, methanol). o.p. (optical purity):92.6%.

(−)-2-cyano-2-methylpentanoic acid may be obtained by using (+)-cis-2-benzylaminocyclohexylmethanol instead of (−)-cis-2-benzylaminocyclohexylmethanol.

EXAMPLE 5

(+)-2-cyano-2-methylpentanoic was prepared through the following steps:

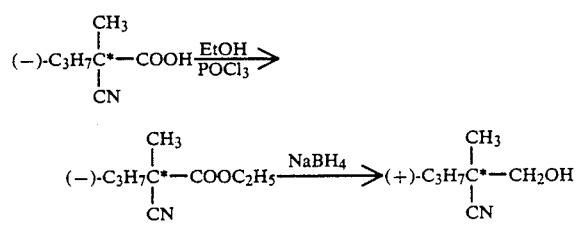

STEP 1

Production of ethyl 2-cyano-2-methylpentanoate 0.30 g (2.1 mM) of (−)-2-cyano-2-methylpentanoic acid was dissolved in 3 ml of dry ethanol. To the mixture under stirring, 0.49 g (3.2 mM) of phosphorus oxychloride was added dropwise. After the reaction for 3 hours at 80° C., 6 ml of 1N-sodium carbonate aqueous solution was added, followed by extraction with diethyl ether. The resultant ether solution was dried on anhydrous sodium sulfate, followed by distilling-off of the solvent and distillation to obtain 0.32 g (1.9 mM) of (−)-ethyl 2-cyano-2-methylpentanoate. Yield:90%, b.p.:110° C./22 mmHg, $[\alpha]_D$ −3.0 degrees, $[\alpha]_{435}$ −4.5 degrees, (c1, methanol)

Step 2

Production of (+)-2-cyano-2-methylpentanol

A solution of 2.28 g(13.5 mM) of (−)-ethyl 2-cyano-2-methylpentanoate in 22 ml of dry tetrahydrofuran was added dropwise to a mixture of 1.14 mg (27.0 mM) of anhydrous lithium chloride and 1.02 mg (27.0 mM) of sodium borohydride under stirring at room temperature. Then, 44 ml of dry ethanol was added thereto, followed by 16 hours of reaction at room temperature. After the reaction, while the reaction mixture was cooled on an ice bath, 10% citric acid was added until the pH reached 4. A white solid recipitated at this time was separated by filtration, and the solvent was removed from the filtrate by reduced pressure distillation. Then, 5 ml of distilled water was added to the product, followed by extraction with dichloromethane. The resultant organic layer was dried on sodium sulfate, followed by distilling-off of the solvent under reduced pressure and further distillation to obtain 9.35 mg(10.6 mM) of (+)-2-cyano-2-methylpentanol. Yield:78.7%, b.p. 110° C.; $[\alpha]_D$ −0.9 degree, $[\alpha]_{435}$ −1.6 degree (c1, CH$_2$Cl$_2$).

EXAMPLE 6

A liquid crystal mixture was prepared by adding 5 wt. parts of the optically active compound according to the above Example 2 to 95 wt. parts of a smectic liquid crystal MORA 8 having a structure as shown below. The liquid crystal mixture showed an SmC* phase, and showed a spontaneous polarization 1.8 times that of MORA 8 alone and a response time of 25 msec, about 60% of that of MORA 8 alone, under the voltage application condition of ±15 V. MORA8

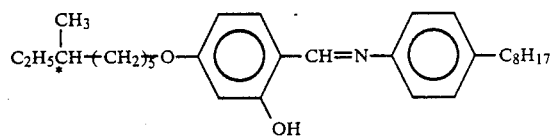

EXAMPLE 7

A glass substrate provided with an ITO transparent electrode film was coated with a polyimide resin precursor (SP-510, mfd. by Toray K.K.), followed by heating at 300° C. for 60 minutes to form a polyimide film. Then, the film was orientation-treated by rubbing. Two glass substrates thus treated were fixed to each other so that their rubbing treated axes crossed each other at right angels, thereby to form a blank cell with a cell gap of 8 microns. The cell was filled with a nematic liquid crystal composition (Lixon GR-63, a biphenyl liquid crystal mixture available from Chisso K.K.) to form a TN (twisted nematic)-type cell. When observed through a polarizing microscope, the TN-type cell showed a fringe pattern due to occurrence of reverse domain.

A liquid crystal composition was prepared by adding 1 wt. part of the optically active compound obtained by the above Example 2 to 99 wt. parts of the above Lixon GR-63 and used for preparation of a TN cell in the same manner as above. As a result of observation through a polarizing microscope, no reverse domain was observed but a uniform nematic phase was observed in the TN cell. From this fact, the optically active compound of the invention was found to be effective for prevention of reverse domain.

EXAMPLE 8

A TN cell was prepared in the same manner as in Example 7 except that the optically active compound, (+)-2-cyano-2-methyl-1-hexanol, used in Example 7 was replaced by an optically active compound, (+)-2-cyano2-methylhexanoic acid, prepared in Example 1. As a result of observation through a polarizing microscope of the TN cell, no reverse domain was observed but a uniform nematic phase was observed.

As described above, according to the present invention, there are provided optically active compounds represented by the formulas [1] and [2] having a cyano group with a large dipole moment directly attached to an asymmetric carbon atom.

Further, by inclusion of at least one species of the optically active compounds, it is possible to prevent the occurrence of a reverse domain in a TN-type liquid crystal composition or to improve characteristics, such as an electric field responsive characteristic, of a chiral nematic liquid crystal or chiral smectic liquid crystal.

What is claimed is:

1. An optically active 2-cyano-2-methyl-1-alkanol represented by the formula:

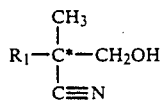 [2]

wherein $R_2$ denotes an alkyl group having 2–10 carbon atoms, and C* denotes an asymmetric carbon atom.

2. A liquid crystal composition, comprising a mesomorphic compound and an optically active 2-cyano-2-methyl-1-alkanol represented by the formula:

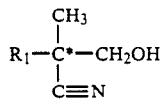 [2]

wherein $R_2$ denotes an alkyl group having 2–10 carbon atoms, and C* denotes an asymmetric carbon atom.

3. An optically active compound according to claim 1, wherein $R_2$ is an alkyl group having 3–10 carbon atoms.

4. An optically active compound according to claim 3, wherein $R_2$ is an alkyl group having 3–8 carbon atoms.

5. An optically active compound according to claim 4, wherein $R_2$ is an alkyl group having 4–6 carbon atoms.

6. A liquid crystal composition according to claim 2, wherein $R_2$ is an alkyl group having 3–10 carbon atoms.

7. A liquid crystal composition according to claim 6, wherein $R_2$ is an alkyl group having 3–8 carbon atoms.

8. A liquid crystal composition according to claim 2, wherein $R_2$ is an alkyl group having 4–6 carbon atoms.

* * * * *

UNITED STATES PATENT AND TRADEMARK OFFICE
CERTIFICATE OF CORRECTION

PATENT NO. : 4,999,130
DATED : March 12, 1991
INVENTOR(S) : HIROYUKI NOHIRA ET AL.

It is certified that error appears in the above-identified patent and that said Letters Patent is hereby corrected as shown below:

ON TITLE PAGE:

AT [75] INVENTORS

"KAZUHIGE YAMAGISHI" should read --KAZUSHIGE YAMAGISHI--.

Signed and Sealed this

Thirteenth Day of August, 1991

Attest:

HARRY F. MANBECK, JR.

Attesting Officer

Commissioner of Patents and Trademarks